United States Patent [19]

Koch

[11] Patent Number: 5,254,686
[45] Date of Patent: Oct. 19, 1993

[54] PROCAINE DOUBLE SALT COMPLEXES

[76] Inventor: Robert Koch, P.O. Box 565, West Jordan, Utah 84084

[21] Appl. No.: 951,662

[22] Filed: Sep. 25, 1992

Related U.S. Application Data

[60] Division of Ser. No. 322,917, Mar. 14, 1989, Pat. No. 5,162,344, which is a continuation-in-part of Ser. No. 46,241, May 4, 1987, abandoned.

[51] Int. Cl.$^5$ ............... C07D 475/00; C07D 473/00; A61K 31/495; A61K 31/415
[52] U.S. Cl. ................. 514/249; 548/303.7; 544/258
[58] Field of Search ........ 514/535, 392, 249; 560/20; 548/453, 303; 544/258

[56]     References Cited
         U.S. PATENT DOCUMENTS

| | | | |
|---|---|---|---|
| 4,010,193 | 3/1977 | Harsanyi et al. | 560/20 |
| 4,956,391 | 9/1990 | Sapse | 514/810 |
| 5,064,858 | 11/1991 | Sapse | 514/536 |

FOREIGN PATENT DOCUMENTS 477822  4/1936  United Kingdom .

*Primary Examiner*—Frederick E. Waddell
*Assistant Examiner*—Raymond J. Henley, III
*Attorney, Agent, or Firm*—Thorpe, North & Western

[57]                ABSTRACT

A procaine acid addition salt, wherein the acid is attached to the diethylamino nitrogen, is complexed with a biologically active organic acid such as a vitamin acid, essential unsaturated fatty acid, $C_4$ to $C_6$ hydroxycarboxylic acid or alpha amino acid in stoichiometric ratios of organic acid to procaine acid addition salt to form a double salt complex wherein the organic acid attaches to the p-amino nitrogen. Such double salt complexes protect the procaine molecule from cholinesterase hydrolysis when orally administered to warm blooded animals allowing the complex to be carried intact to the site of damaged cells and across the cell membrane where the double salt complex is disassociated in the cell releasing the organic acid and procaine for cellular repair and regeneration. Procaine hydrochloride is the preferred procaine salt. Preferred acids are citric and vitamin acids including nicotinic acid, ascorbic acid, biotin and folic acid.

8 Claims, No Drawings

PROCAINE DOUBLE SALT COMPLEXES

This application is a divisional of copending application Ser. No. 07/322,917 filed Mar. 14, 1989, now U.S. Pat. No. 5,162,344 which is a continuation in-part of Ser. No. 07/046,241 filed May 4, 1987 and now abandoned.

This invention relates to double salt complexes between procaine salts and various biologically active organic acids. More particularly, this invention relates to double salt complexes between a procaine salt and one or more biologically active acids which exhibit vitamin or other useful biological activity.

Procaine is a widely known local anesthetic and is the 2-diethylaminoethyl ester of p-aminobenzoic acid. In its hydrochloride salt form, it is soluble in water and commonly used under its tradename Novocaine. Other salts are also known such as the nitrate, butyrate, borate and hydrobromide salts. Procaine hydrochloride is the most commonly used salt and was discovered in about 1905 as a replacement for the highly addictive local anesthetic, cocaine. By 1960 its use in the United States alone had reached about 377,000 pounds.

Once absorbed, the procaine hydrochloride salt is rapidly hydrolyzed by plasma cholinesterase into p-amino benzoic acid (PABA) and diethylaminoethanol (DEAE).

PABA is a well known vitamin which is often considered necessary for growth of poultry, for the growth of healthy intestinal flora, and for the maintenance of a normal fur coat in fur producing animals. It has also been suggested as a vitamin which functions in the processes dealing with skin and hair pigmentation. Also, PABA is an intermediate in the preparation of other vitamins such as folic acid, biotin, niacin and $B_{12}$.

DEAE is also biologically active. It is closely related to its adjacent homolog dimethylaminoethanol (DMAE) which is precursor of the vitamin choline. DEAE also participates in the synthesis of choline and acetylcholine. DEAE has also been reported to produce mental stimulation, mild euphoria and, unlike other mental stimulants such as amphetamines, has no adverse side effects such as depression.

For many years, procaine, and procaine compositions used alone or stabilized by benzoic acid have been studied for their use in the treatment of depression and/or use in gerontology. There have been numerous studies and reports published on the advantages of procaine therapy. Procaine formulations known as or marketed under tradenames GH3 or Gerovital H3 as well as other procaine formulations are widely marketed outside the United States without prescription. Detailed information on various clinical studies of procaine formulations in the treatment of aging and depression are contained in a book by Herbert Bailey, "GH3-Will it Keep You Young Longer?", 1977, Bentham Books, Inc., New York, N.Y.

Studies have shown that both procaine and PABA act at the level of cell membrane metabolism. However, one of the disadvantages of administering procaine, either orally or by injection, is that it is hydrolyzed so rapidly by the cholinesterase enzyme that it does not penetrate or cross the cell membrane as effectively as is desired. The half life of procaine in human serum at 37° C. is stated to be only about 0.52 to 0.80 of a minute. It has been shown that PABA and DEAE administered as a mixture do not possess the same biological activity as does procaine.

It would therefore be desirable to have a formulation that would protect the procaine molecule from hydrolysis by the cholinesterase enzyme while not interfering with the ability of procaine to penetrate the cell membrane wall. Solutions containing 1.3–6.5 moles of caffeine per mole of procaine have been shown to inhibit procaine hydrolysis in aqueous solutions. Also, aqueous solutions of about 0.1 mole benzoic acid per mole of procaine have been suggested as inhibiting hydrolysis. However, there appears to be no definitive studies showing that either caffeine or benzoic acid in serum solutions will inhibit the cholinesterase enzyme from rapidly hydrolyzing the procaine molecule. Moreover, caffeine is a CNS stimulant and its coadministration with procaine may be contraindicated. Also, benzoic acid, although of relatively low toxicity, is a bacterioside and not readily metabolized. It combines with glycine as a conjugate forming hippuric acid which is removed through the urine. Because of its properties, benzoic acid has not been reacted with procaine in stoichiometric amounts. Thus, even if it were to protect procaine from rapid hydrolysis, it would only protect a minor amount.

German Offenlegungsschrift 26 22 622, published Dec. 9, 1976, teaches simple salts formed by reacting procaine base with nicotinic acid. This nicotinate salt is said to have the capacity to permeate, cell membranes, particularly nerve cells, and become involved in cell regeneration metabolism. As such, the salt is said to be the active ingredient in treatment of the aged, particularly in improving learning potential and memory capacity. However, the product prepared from the combination of procaine base and nicotinic acid is a single salt having a different structure from the double salts claimed herein. When procaine base is reacted with an acid such as nicotinic acid, the acid associates on the diethylamino nitrogen as shown by Formula I:

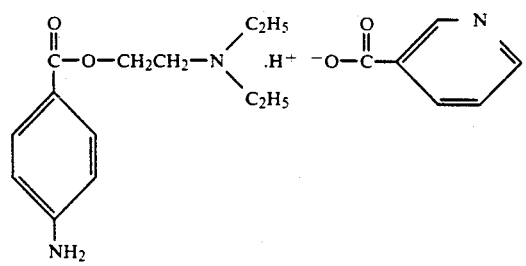

The nicotinate salt of Formula I is a vitreous amorphous compound having no defined melting point. If one then attempts to form a hydrochloride salt of the compound of Formula I the HCl associates with the pyridinyl nitrogen of the nicotinic acid forming the compound of Formula II:

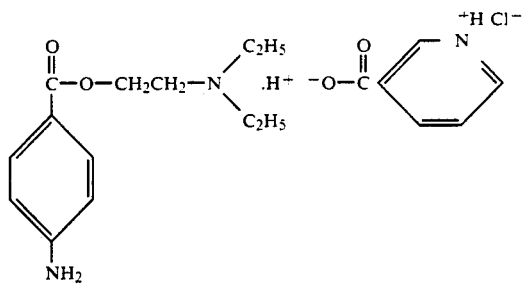

The compound of Formula II is a white crystalline compound with a melting point of between about 218°–223° C. with some decomposition.

OBJECTS AND BRIEF SUMMARY OF THE INVENTION

It is an object of the present invention to provide a double salt complex formed by the combination of a procaine salt and a beneficial biologically active organic acid which protects the procaine from rapid hydrolysis by cholinesterase.

It is also an object of the present invention to provide double salt complexes of procaine salts with bioactive organic acids which readily cross the cell membrane barrier and assist in cellular repair.

Another object of this invention is to provide double salt complexes of a procaine salt and vitamin or other biologically useful acids wherein the double salt complex serves as a carrier means for assisting the transfer of the acid across the cell membrane.

These and other objects may be accomplished by complexing a procaine salt, preferably the hydrochloride, with at least a stoichiometric amount of one or more bioactive acids. These acids are selected from the group consisting of vitamin acids, essential unsaturated fatty acids, $C_4$ to $C_6$ hydroxy carboxylic acids, and alpha amino acids. Preferably, these acids will be selected from the group consisting of nicotinic acid, folic acid, biotin, citric acid and ascorbic acid. Other bioactive acids which can also be used include pantothenic acid, orotic acid, aspartic acid, succinic acid, fumaric acid, gluconic acid, methionine, tryptophane, tyrosine, glycine, dimethylglycine, glutamic acid, gamma linolenic acid and linoleic acid.

These acids form stable double salt complexes which are thought to remain primarily intact when being orally ingested and pass through the digestive tract, are transported through mucosal membranes and into the blood where they are transported to the cell site where the complexes are separated into their individual components and utilized in the manner taught in the prior art or for cellular repair.

DETAILED DESCRIPTION OF THE INVENTION

Complexes between a procaine salt and the bioactive acids can be made by combining, in stoichiometric ratios, the complexing acid with the procaine salt in suitable solvents such as water, water-alcohol mixtures, acetone or acetone-alcohol mixtures and heat or vacuum concentrating depending on stability.

When a salt is formed from procaine base and an acid, such as hydrochloric acid, the acid associates with the diethylamino nitrogen to form the acid addition salt shown in Formula III:

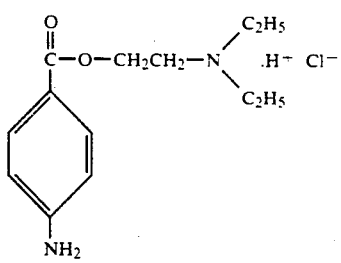

By combining the hydrochloride salt of Formula III with stoichiometric amounts of a vitamin acid, such as nicotinic acid, the double salt procaine hydrochloride nicotinate is formed as shown in Formula IV:

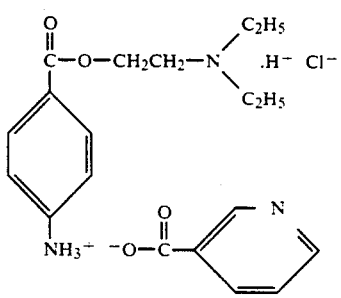

This is a totally different compound from the procaine nicotinate illustrated in German offenlegungsschrift 26 22 622 referred to above. The double salt of Formula IV has the HCl bonded to the diethylamino nitrogen with the nicotinic acid associating on the p-amino nitrogen of the p-amino benzoic acid portion of the molecule. This compound is a well defined white crystalline salt having a mole weight of 395.38 and a melting point of between 195° and 200° C. Because of its distribution of electrical charges, the compound of Formula IV tends to cause the complex to double back upon itself causing a tighter structure which, in turn, increases the protection of the ester linkage between the p-amino benzoic acid and diethylaminoethanol portions of the procaine molecule. This in turn provides greater protection against enzymatic cleavage of the procaine molecule. The double salt of Formula IV has a greater positive ion effect because of double ionization. This increases cell membrane polarization and effective net membrane charge. This increases the transfer rate of the complex across the membrane into the cell either through receptor cite mediated transport or through endocytosic transfer.

The other complexes of procaine HCl with the organic acids mentioned, because of the organic acids linking to the p-amino nitrogen, produces the same type of increased protection of the ester linkage as just described. These double salts of procaine HCl, with the various organic acids and/or other possible biologically active compounds that show an affinity to complex with the procaine HCl molecule, provides an abundance of non-toxic cellular nutrients that can provide either general or specific nutrition to damaged, diseased cells that can be tailored to address specific or general problems.

Whatever double salt complex is formed using a procaine salt and an organic acid, it will fall within the scope of the following Formula V:

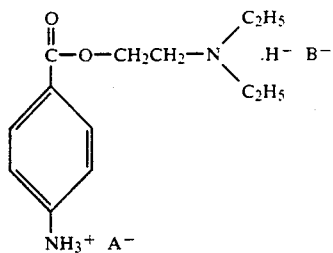

wherein B is an anion of an acid selected from the group consisting of hydrochloric acid, nitric acid, butyric acid, boric acid and hydrobromic acid and A is the anion of biologically beneficial organic acids selected from the group consisting of vitamin acids, essential unsaturated fatty acids, $C_4$ to $C_6$ hydroxycarboxylic acids, and alpha amino acids. Within that group, a preferred anion for B is the hydrochloride ion and the preferred anion combination for A is made up of anions from acids selected from the group consisting of nicotinic acid, folic acid, biotin, citric acid, ascorbic acid, pantothenic acid, succinic acid, fumaric acid, gluconic acid, linolenic acid, linoleic acid, methionine, tryptophane, tyrosine, glycine, dimethylglycine and glutamic acid. Most particularly preferred within the A anion grouping are anions from acids selected from the group consisting of nicotinic acid, folic acid, biotin, ascorbic acid and citric acid.

Illustrative complexes of vitamin acids or citric acid within the above groupings are contained in Table-I as follows:

TABLE I

| FORMULA NO. | STRUCTURE | MOLE WEIGHT |
|---|---|---|
| VI | Procaine HCl Folic Acid Double Salt Complex | 713.68 |
| VII | Procaine HCl Biotin Double Salt Complex | 516.59 |
| VIII | Procaine HCl Ascorbic Acid Double Salt Complex | 488.41 |

TABLE I-continued

| FORMULA NO. | STRUCTURE | MOLE WEIGHT |
|---|---|---|
| IX | Procaine HCl Citric Acid Double Salt Complex | 464.41 |

Similar complexes may be formed using the other acids such as orotic acid, aspartic acid, succinic acid, fumaric acid, gluconic acid, pantothenic acid, linolenic acid, linoleic acid and various alpha amino acids such as tyrosine, tryptophane, methionine, glycine, dimethylglycine and glutamic acid.

The double salt complex is formed beginning with a procaine salt, i.e. the hydrochloride bonded to the diethylamino nitrogen. The pH for forming the double salt will depend upon the particular organic acid being but will generally be in the acid range of about 2.5 to 6.8.

The most preferable complexes are those formed from complexing a mixture of various vitamin acids with procaine hydrochloride to form an intricate composition consisting of procaine hydrochloride complexed with various acids and also, wherein the various complexed double salt molecules are crosslinked with each other. For example, when using a complexing acid mixture containing an excess of citric and/or folic acids, these acids most probably cause additional crosslinking between the various complexes due to the trihydric nature of the citric acid and the dihydric nature of the folic acid.

Thus, while the exact structural formula of the complexes formed from a mixture of organic acids is subject to variation, it is known that there is a chemical interaction between the various procaine double salt complexes. This is also manifest in the demonstrated biological activity. Mixtures of a single procaine salt, such as procaine hydrochloride, and the various acids do not provide the same result as does administration of the double salt complexes formed from the same acids. Taking the reaction a step further, crosslinked complexes formed by the interaction between various double salt complexes, in many cases, have enhanced biological activity over an isolated double salt complex made of only a single biologically active organic acid.

When selecting the vitamin acid or mixture of vitamin acids to utilize in forming a procaine double salt complex, it is often advantageous to keep in mind the recommended amount of vitamin acid to be consumed on a daily basis, i.e., the U.S. Recommended Daily Allowance (U.S. RDA) as well as the dosage of procaine desired.

The following examples illustrate the methods of preparing procaine salt-vitamin acid complexes.

EXAMPLE I

Into a heated round bottom flask was placed 360 mls of distilled water which was heated to 90°-95° C. To the heated water was added 1.02 grams (0.0023 moles) of USP folic acid and stirred until dissolved. There was then added 272.27 grams (1 mole) of procaine hydrochloride which was dissolved. The heat was then turned off and there was added in succession, with each ingredient being dissolved into the mixture before adding the next, 42.6 grams (0.346 moles) of USP nicotinic acid, 1.05 (0.0043 moles) grams of d-biotin USP, 68.86 grams (0.391 moles) of ascorbic acid USP, 68.78 grams (0.358 moles) of USP citric acid, 64.00 grams USP potassium chloride and 75.45 grams of USP magnesium sulfate ($MgSO_4 \cdot 7H_2O$).

To this hot mixture was added a proper amount of microcrystalline cellulose mixed with 16 gm USP magnesium oxide as a carrier and the mixture was dried at 55° C. for 24 hours. A granular mixture was obtained to which was added stearic acid as a lubricant. This mixture was formed into tablets weighing between 500 to 510 milligrains, each tablet containing 100 mg. of procaine hydrochloride complexed with 16 mg. nicotinic acid, 0.4 mg. folic acid, 0.3 mg. biotin, 25 mg. ascorbic acid, 25 mg. citric acid, 11 mg. potassium and 4 mg. magnesium.

The ratios of ingredients making up the procaine hydrochloride complexes were determined by the current U.S. RDA's for the vitamin ingredients.

PREPARATION OF INDIVIDUAL PROCAINE-VITAMIN ACID COMPLEXES

In forming the following complexes, the solvents utilized were determined by the solubility of the reactive ingredients used. When using procaine HCl, these complexes are best formed using water, water-ethanol or water-acetone combinations.

When tablets are to be formed, it may be more efficient not to isolate the complex from the solvent, although that can be done if desired. However, it may be preferable to add the excipients to the complex in the solvent with mixing to form a granulated mixture directly from the solvent.

EXAMPLE II

1:1 Complex of Procaine HCl and Nicotinic Acid-(Procaine HCl Nicotinate)

To 50 mls. of boiling water was added 27.2 grams (0.1 mole) of procaine HCl with stirring until completely dissolved. With stirring was added 12.3 grams (0.1 mole) of nicotinic acid. This mixture was heated at the boiling point until clear. The solution was allowed to cool and a white crystalline precipitate formed which was separated in a Buchner funnel and washed twice with 5.0 aliquots of cold distilled water. The product was dried to fine white crystals which were moderately soluble in water and 95% ethanol. The crystals had a melting point between 195°-200° C. In contrast, a 1:1 molar mixture of procaine HCl and nicotinic acid melts at 145°-150° C.

EXAMPLE III

1:1 Complex of Procaine HCl and Folic Acid (Procaine HCl Folate)

Into 105 mls of boiling water was dissolved 13.6 grams (0.05 mole) of procaine HCl. To this solution was slowly added in 2 to 4 gram increments 22 grams (0.05 mole) of folic acid. Each folic acid increment added was dissolved before the next increment was added. The solution was cooled and the precipitate formed was filtered and dried. A reddish/orange crystalline product was obtained which had no melting point. The crystals darken and char above 220° C.

EXAMPLE IV

1:1 Complex of Procaine HCl and Biotin (Procaine HCl Biotinate)

Into a hot solution of 50 mls of ethanol and 30 mls of water was dissolved 2.72 grams (0.01 mole) of procaine HCl. To this was added 2.44 grams (0.01 mole) of biotin and heat was maintained until the ingredients reacted and the solution cleared. On cooling, crystallization took place easily. White crystalline platelets were filtered, washed and dried. These crystals were partly soluble in water and ethanol and had a melting point of about 212°-215° C.

The procaine double salt complexes formed function by taking advantage of the ability of the procaine double salt to pass through the cell membrane, particularly through damaged or diseased cell membranes. The complexing acids added to the pamino group initially act to sterically protect the procaine molecule from being attacked by the cholinesterase enzyme in the blood. Therefore, the procaine ester molecule remains intact for sufficient time to allow it to be transferred into cells throughout the body. Moreover, the procaine acts as a transporting agent and helps to carry the complexing organic acid into the cells also.

Once in the cell, the complex dissociates into the various complexing acids and procaine. The procaine hydrolyses into diethylaminoethanol (DEAE) and para-aminobenzoic acid (PABA). The PABA helps to increase ATP production. The DEAE is split by action of a dealkylating enzyme into ethanolamine. Further enzymatic oxidation of the ethyl groups split from the DEAE results in the formation of two acetyl groups which are transferred into the ion pool or utilized for the preparation of acetylcholine. The ethanolamine functions as a precursor for the preparation of various phospholipids. The ethanolamine is reacted with a phosphatidyl radical to form phosphatidyl ethanolamine, also known as phosphatidyl colamine, which is present in the brain and is the major component of the inner lipid layer of all cell membranes. Through the action of S-adenosine methionine, a methyl, donor in transmethylation reactions, the phosphatidyl ethanolamine is further converted to phosphatidyl choline, also more commonly known as lecithin, which is the major component of the outer lipid layer of all cell membranes. In addition, ethanolamine can be methylated with S-adenosine methionine to form choline which reacts with acetyl groups to form acetyl choline which is responsible for transmission of nerve unpulses.

The stabilization of procaine in double salt complex form to enable it to be transported directly to the cells where it is broken down into vitamin acids, DEAE and PABA is of extreme importance in cellular repair. Lecithin and other phospholipids, for example, are generally hydrolyzed in the small intestine by enzymatic action and thus fail to reach the site of damaged cells where they are needed for cell membrane repair. Thus, procaine, if kept intact, functions in a manner similar to a vitamin being a viable source of PABA and DEAE to damaged cells. Damaged cells often have difficulty in transferring nutrients across the cell membranes. However, the procaine double salt complexes of the present invention are believed to be efficiently transferred intact across damaged membranes bringing to the cells sources of vitamins, DEAE and PABA for immediate cell regeneration and repair.

As the membrane repair progresses, the functions of the cellular sodium and calcium pumps are increased, removing unwanted excesses of these minerals from the cell. Preferably, the compositions of this invention are formulated with sources of potassium and magnesium. The potassium and magnesium replace the sodium and calcium in the cells resulting in higher membrane potentials. This, in turn, improves feeding and the function of enzyme systems in the cell. These changes, along with others not understood, bring about a cellular repair process which inhibits cell degeneration and, in some cases, is believed to cause a reversal in many cell degenerative processes.

One particular advantage of the present invention is its low toxicity. The oral toxicity of the compositions prepared in Example I is extremely low. In rabbits, the LD50 is in excess of 800 mg/kg of body weight. Based on procaine HCl content of the complex, a dose easily supported by animals is 100 mg/kg of body weight with an acceptable therapeutic dose being 1.66 mg/kg. That is a safety factor of at least 60. Moreover, since the active ingredients are vitamins or break into vitamin type compounds, there is almost total absence of side effects. Hence, as cellular repair agents, the complexes of procaine salts and vitamin or other type acids are safe, relatively free from side effects and provides an excellent means to provide the cell with the needed components to instigate the cellular repair processes. Although single double salt complexes are effective in all cell types of treatment, the composition of Example I has been found to be generally more effective in providing cellular repair in a larger variety of conditions.

Thirty people (10 males and 20 females) ranging in age from 27 to 71 years, having diagnosed rheumatoid arthritis, were treated with the combined complex of Example I. All subjects had been arthritic for a number of years with some of the older subjects being crippled with calcified lumps about the finger joints. Each subject was treated with a starting dosage of 2 100 mg. tablets (based on procaine HCl) per day taken on an empty stomach. The tablets were administered six to eight hours apart. Three subjects noticed reduced pain and greater joint mobility within the first three days. By the end of the first month twenty seven subjects experienced almost no pain and greater movement of the joints. Starting the second month the dosage was increased to 4 100 mg. tablets (based on procaine HCl) per day taken on an empty stomach. Two tablets were taken in the morning and two were taken six to eight hours later in the afternoon. By the end of three months twenty eight subjects were pain free and had discontinued taking pain medication. The older subjects with calcified joint nodules noted that the nodules reduced in size and further noted improvement in hand movement and gripping ability. At the end of one year twenty nine subjects continued to experience no pain and had improved joint mobility. One female subject dropped out due to an apparent allergy to procaine HCl.

While the results in the above study are based on subjective determinations reported by the subjects it does demonstrate the positive effect double salt complexes of procaine HCl has on subjects suffering from rheumatoid arthritis. Other benefits were also noticeable. Of the thirty subjects who participated in the above study, three of the females suffered PMS which was controlled while taking the procaine HCl double salt complexes. All subjects reported noting unproved energy levels, improved sleep habits and less tendency for depression. Two subjects were taking anti-depressant medication and were able discontinue such medication while taking the procaine HCl double salt complexes.

The above description is considered as sufficient to teach one skilled in the art how to make the compositions and practice the invention. However, other embodiments not specifically disclosed will be obvious to one engaged in this art. Therefore, the following claims are meant to include all operable embodiments of the invention within the scope of the claims, whether or not specifically disclosed in the specification, and their functional equivalents.

I claim:

1. A double salt complex formed from the reaction between stoichiometric amounts of a procaine salt and a vitamin acid, said double salt complex having the formula:

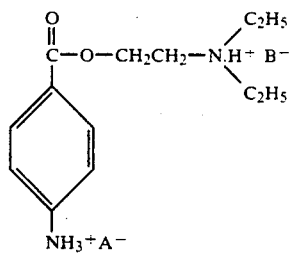

where B is the anion of an acid selected from the group consisting of hydrochloric, hydrobromic, boric, nitric, and butyric acids and A is selected from the group consisting of the anion of folic acid and the anion of biotin.

2. A double salt complex according to claim 1 wherein B is the hydrochloride anion.

3. A double salt complex according to claim 2 wherein A is the anion of folic acid.

4. A double salt complex according to claim 2 wherein A is the anion of biotin.

5. A method of promoting cellular repair to damaged cells a warm blooded animal which comprises orally administering to said animal an effective amount of a double salt complex formed from the reaction between stoichiometric amounts of a procaine salt and a vitamin acid, said double salt complex having the formula:

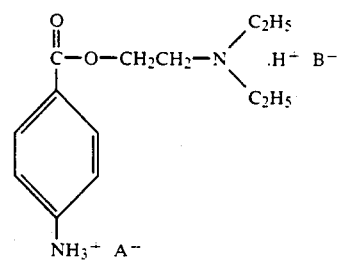

where B is the anion of an acid selected from the group consisting of hydrochloric, hydrobromic, boric, nitric, and butyric acids and A is selected from the group consisting of the anion of folic acid and the anion of biotin.

6. A method according to claim 5 wherein B is the hydrochloride anion.

7. A method according to claim 6 wherein A in the double salt complex is the anion of folic acid.

8. A method according to claim 6 wherein A in the double salt complex is the anion of biotin.

* * * * *